(12) United States Patent
Li

(10) Patent No.: US 8,210,345 B2
(45) Date of Patent: Jul. 3, 2012

(54) DISPENSING CONTAINER OF PROBE COVERS AND ASSEMBLY THEREOF

(75) Inventor: Liang-Yi Li, Hsinchu (TW)

(73) Assignee: Actherm Inc, Hsinchu (TW)

( * ) Notice: Subject to any disclaimer, the term of this patent is extended or adjusted under 35 U.S.C. 154(b) by 0 days.

(21) Appl. No.: 12/635,799

(22) Filed: Dec. 11, 2009

(65) Prior Publication Data

US 2010/0147720 A1    Jun. 17, 2010

Related U.S. Application Data

(63) Continuation-in-part of application No. 12/566,259, filed on Sep. 24, 2009, now abandoned.

(30) Foreign Application Priority Data

Dec. 17, 2008  (WO) ............... PCT/CN2008/002024
Aug. 21, 2009  (TW) .............................. 98128154 A

(51) Int. Cl.
*B65D 85/38*  (2006.01)
*B65H 1/00*  (2006.01)
(52) U.S. Cl. .................. 206/306; 206/305; 221/198
(58) Field of Classification Search ............ 206/306; 221/198, 226, 236, 279, 239, 244, 251, 303, 221/59, 61, 63; 374/158
See application file for complete search history.

(56) References Cited

U.S. PATENT DOCUMENTS

| | | | | |
|---|---|---|---|---|
| 3,628,692 A | * | 12/1971 | Blatz | 221/70 |
| 3,709,402 A | * | 1/1973 | Templeton et al. | 221/33 |
| 4,993,424 A | * | 2/1991 | Suszynski et al. | 600/549 |
| 5,100,018 A | | 3/1992 | Rosati et al. | |
| 6,123,454 A | * | 9/2000 | Canfield et al. | 374/158 |
| 6,840,402 B2 | | 1/2005 | Lin et al. | |

FOREIGN PATENT DOCUMENTS

| | | |
|---|---|---|
| CN | 2433223 Y | 6/2001 |
| JP | 2000041955 A | 2/2000 |
| JP | 2005288190 A | 10/2005 |
| TW | 333172 U | 6/2008 |
| TW | 333560 U | 6/2008 |

* cited by examiner

*Primary Examiner* — J. Gregory Pickett
*Assistant Examiner* — Ernesto Grano
(74) *Attorney, Agent, or Firm* — Ming Chow; Sinorica, LLC

(57) ABSTRACT

A dispensing container, mounted on a supporter, comprises a hollow body made of a flexible material for accommodating ear thermometer probe covers, where the hollow body has one end formed with an access opening for allowing a probe of an ear thermometer to insert into an upmost probe cover in the hollow body. Each of the probe covers has the open end provided with at least a flange that radially extends outward from the open end, where the hollow body has a substantially rectangular section that has major edges smaller than a diameter of the flange of one probe cover in length, so that when the probe covers are placed into the hollow body, each inner wall of the hollow body is deformed to tangent to the flanges of the probe covers, so as to keep the probe covers securely in the hollow body.

11 Claims, 6 Drawing Sheets

DISPENSING CONTAINER OF PROBE COVERS AND ASSEMBLY THEREOF

CROSS-REFERENCE TO RELATED APPLICATIONS

This application is a Continuation-in-part of U.S. patent application Ser. No. 12/566,259 now abandoned entitled "DISPENSING CONTAINER FOR PROBE COVERS AND MANUFACTURING METHOD THEREOF" filed on Sep. 24, 2009 which claimed a priority to PCT/CN2008/002024, filed on Dec. 17, 2008.

The current application also claims a priority to the foreign patent application in Taiwan TW098128154, filed on Aug. 21, 2009.

BACKGROUND OF THE INVENTION

1. Technical Field

The present invention relates to a dispensing container for probe covers of ear thermometers and an assembly for such dispensing container. More particularly, the present invention relates to a dispensing container that receives the probe covers each of which has an open end provided with a flange extending outward from the open end, and an assembly for such dispensing container.

2. Description of Related Art

The conventional dispensing container for storing and providing probe covers of ear thermometers is not convenient in use because its users, e.g., medical workers, have to take out the probe covers from the dispensing container and then assemble the probe covers to the measuring probes of ear thermometers manually. Particularly, the infrared ear thermometers need to work with probe covers to prevent infection and maintain cleanness of the measuring probes. Although some prior art devices, such as those disclosed in U.S. Pat. Nos. 4,993,424, 5,100,018, and 6,840,402, enable automatic feed for assembling probe covers to ear thermometers and have been used in medical facilities, their mechanical complexity and bulkiness nevertheless inconvenience users in both installing the probe covers into the feeding mechanisms and dispatching the probe covers from the feeding mechanisms. Besides, there is a commercially available dispensing container for probe covers that has a lateral side to be torn open so as to form an opening through which an ear thermometer gets access to the probe covers stored in the dispensing container. However, this dispensing container is disadvantaged by its complicated operation and loss of package integrity once the opening is formed, which exposes the probe covers to the air and, consequently, to contamination.

SUMMARY OF THE INVENTION

To address the shortcomings of the prior art, the present invention proposes a dispensing container and a dispensing assembly. The dispensing container has a hollow body for accommodating a plurality of stacked ear thermometer probe covers, the hollow body having one end formed with an access opening for allowing a probe of an ear thermometer to insert into one of the probe covers positioned in the hollow body, and having another end opposite to the access opening formed with a base. Each of the ear thermometer probe covers has a close end and an opposite open end. The ear thermometer probe covers are such stacked and accommodated in the hollow body that the open ends of the ear thermometer probe covers are posed to face the access opening. Each of the ear thermometer probe covers has the open end provided with at least a flange that radially extends outward from the open end. In addition, the hollow body of the dispensing container has an approximately rectangular section, and major edges of the rectangular section are smaller than a diameter of the flange of the ear thermometer probe cover in length.

Therefore, it is a primary objective of the present invention to provide a dispensing container comprising a hollow body with such an approximately rectangular section that has major edges smaller than a diameter of the flange of each ear thermometer probe cover in length so that when the ear thermometer probe covers are placed into the hollow body, the hollow body made of flexible material has four lateral walls restorably deformed to tangent to the flanges of the ear thermometer probe covers so as to allow the lateral walls of the hollow body to clamp the flanges of the ear thermometer probe covers tightly, and thus the clamping force prevents the ear thermometer probe covers unintentionally drop-off from the dispensing container.

It is a secondary objective of the present invention to provide a dispensing container where a pair of retaining portions are provided at opposite inner lateral walls of the hollow body of the dispensing container and are provided for retaining the flange of the bottommost ear thermometer probe cover.

Besides, the present invention proposes a dispensing assembly, which includes a dispensing container and a supporter, wherein the dispensing container has a hollow body made of a flexible material for accommodating a plurality of stacked ear thermometer probe covers, the hollow body having one end formed with an access opening for allowing a probe of an ear thermometer to insert into one of the probe covers positioned in the hollow body, and having another end opposite to the access opening formed with a base. Each of the ear thermometer probe covers has a close end and an opposite open end. The ear thermometer probe covers are such stacked and accommodated in the hollow body that the open ends of the ear thermometer probe covers are posed to face the access opening. Each of the ear thermometer probe covers has the open end provided with at least a flange that radially extends outward from the open end. The supporter includes a pair of guiding portions extending lengthwise from a bottom of the supporter to an open portion of the supporter for guiding the dispensing container. In addition, the hollow body of the dispensing container has an approximately rectangular section, and major edges of the rectangular section are smaller than a diameter of the flange of the ear thermometer probe cover in length, so that when the ear thermometer probe covers are placed into the hollow body, the hollow body made of flexible material has lateral walls each of which is deformed to tangent to the flange of each ear thermometer probe cover.

Therefore, it is a primary objective of the present invention to provide a dispensing assembly where a pair of tab portions of the base of the hollow body and a pair of guiding portions settled in the supporter with a predetermined interval therebetween are provided. When the dispensing container is mounted on the supporter, outer surfaces of the guiding portions may contact the tab portions and inner surfaces of lateral walls of the hollow body so as to generate a friction. Therefore, the friction prevents the dispensing container unintentionally disassembling from the supporter after they are assembled.

It is a secondary objective of the present invention to provide a dispensing assembly where a pair of guiding portions settled in the supporter and inner lateral walls of a hollow body corresponding to the guiding portions are provided. When the dispensing container is mounted on the supporter, outer surfaces of the guiding portion may contact inner surfaces of lateral walls of the hollow body so as to generate a friction. Therefore, the friction prevents the dispensing container unintentionally disassembling from the supporter after they are assembled.

It is still another objective of the present invention to provide the aforesaid dispensing assembly, wherein a magnitude of the friction is determined by a predetermined interval between the two guiding portions in the supporter.

It is yet another objective of the present invention to provide the aforesaid dispensing assembly, wherein when the dispensing container is mounted on the supporter, chamfered portions of the guiding portions of the supporter abut against the flange of the bottommost ear thermometer probe cover, so that when the dispensing container is pushed downward along the lengthwise direction of the supporter, the relative displacement between the dispensing container and the supporter takes place and makes the access opening of the dispensing container move downward, thereby facilitating access of the ear thermometer probe covers.

BRIEF DESCRIPTION OF THE DRAWINGS

The invention as well as a preferred mode of use, further objectives and advantages thereof will be best understood by reference to the following detailed description of illustrative embodiments when read in conjunction with the accompanying drawings, wherein.

DETAILED DESCRIPTION OF THE PREFERRED EMBODIMENTS

Figure 1A:
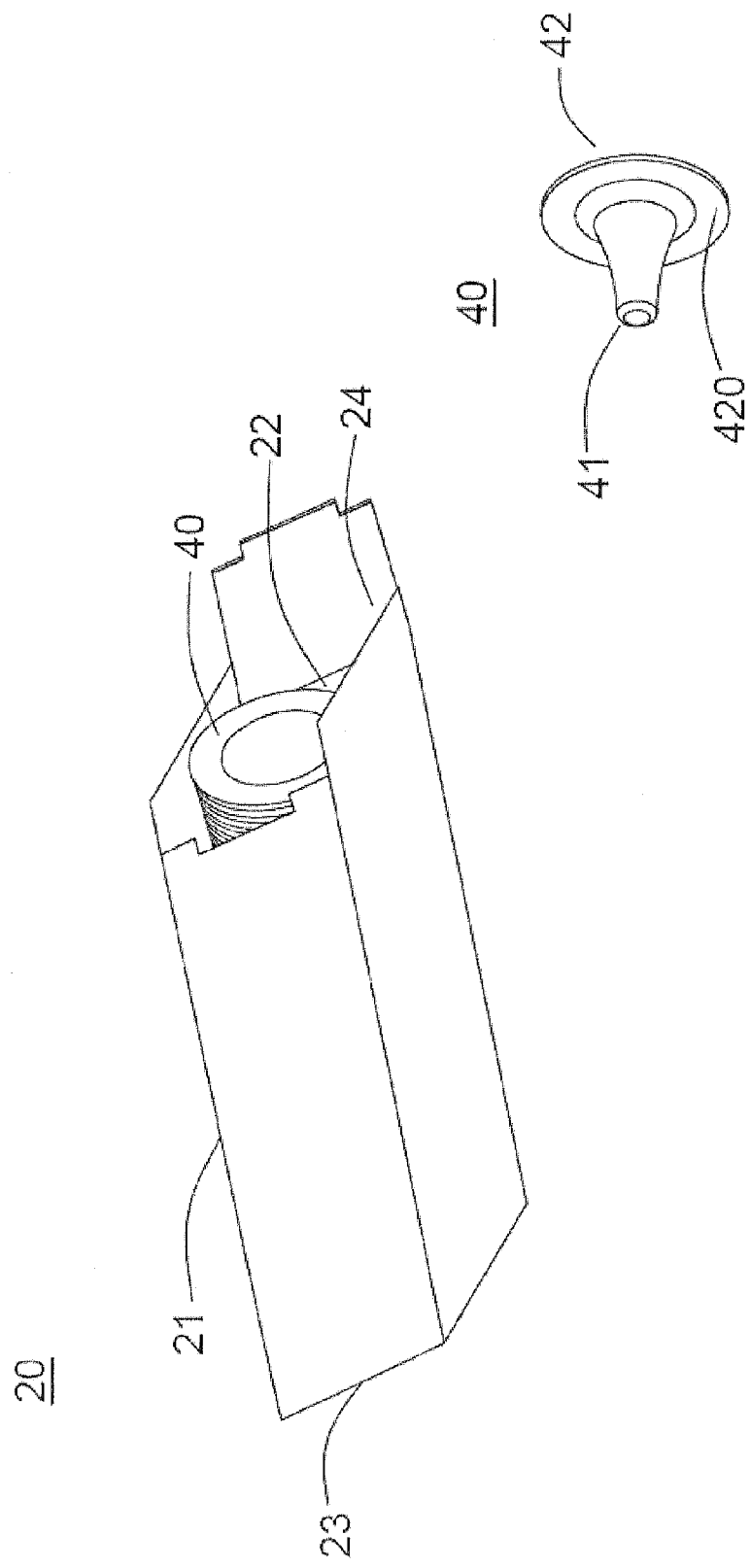
FIG. 1A is a schematic drawing according to a first preferred embodiment of the present invention, showing a dispensing container and ear thermometer probe covers received therein.
Figure 1B:
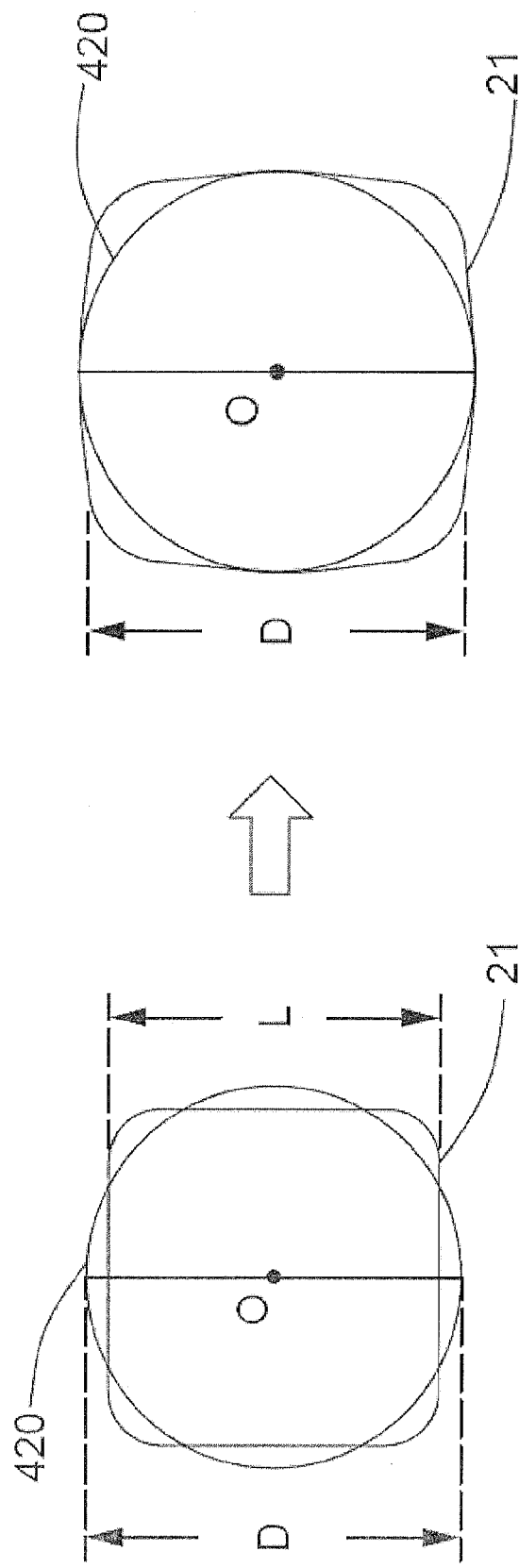
FIG. 1B are end views of the dispensing container according to the first preferred embodiment of the present invention, showing the restorable deformation of the dispensing container before and after a said ear thermometer probe cover is placed therein.

Please refer to FIG. 1A for a dispensing container 20 according to a first preferred embodiment of the present invention. The dispensing container 20 may be mounted on a supporter (not shown) to get positioned. The dispensing container 20 includes a hollow body 21 made of a flexible material for accommodating a plurality of stacked ear thermometer probe covers 40. The dispensing container 20 has one end formed with an access opening 22 for allowing a probe of an ear thermometer (not shown) to insert into the hollow body 21 and access the ear thermometer probe cover 40 positioned upmost. The dispensing container 20 further has another end opposite to the access opening 22 formed with a base 23. Each of the ear thermometer probe covers 40 has a close end 41 and an open end 42 opposite to the close end 41. The ear thermometer probe covers 40 are such stacked and accommodated in the hollow body 21 that their open ends 42 are posed to face the access opening 22. In addition, each of the ear thermometer probe covers 40 has the open end 42 provided with at least a flange 420 that radially extends outward from the open end 42. Referring to FIG. 1B, which provides end views of the dispensing container 20, the hollow body 21 has an approximately rectangular transverse section. As shown in the left part of FIG. 1B, the ear thermometer probe cover 40 is now outside the hollow body 21. It is obvious that the major edges L of the rectangular section of the hollow body 21 is smaller than a flange diameter D of the ear thermometer probe cover 40 in length. When the ear thermometer probe cover 40 is placed into the hollow body 21 of the dispensing container 20, the flexible material of the hollow body 21 allows four lateral walls of the hollow body 21 to be pushed outward by the flange 420 of the ear thermometer probe cover 40 and restorably deform, as shown in the right part of FIG. 1B, so that the four inner lateral walls of the hollow body 21 closely contact the flanges 420 of the ear thermometer probe covers 40, thereby properly holding the ear thermometer probe covers 40 inside the hollow body 21 without unintentionally coming off.

In the first preferred embodiment, the hollow body 21 is made of paper or plastic so as to provide desired flexibility. The dispensing container 20 may further comprise an upper cover 24 for closing the access opening 22, thus preventing the ear thermometer probe covers 40 received therein from being directly exposed outside and getting contaminated. In addition, referring to FIG. 1C, the base 23 of the hollow body 21 includes a pair of tab portions 231 to be bent toward the hollow body 21 and a lower cover 232. Therein, the lower cover 232 can close the hollow body 21 to prevent the close end 41 of the ear thermometer probe cover 40 positioned bottommost from being directly exposed outside and getting contaminated.

Figure 2:
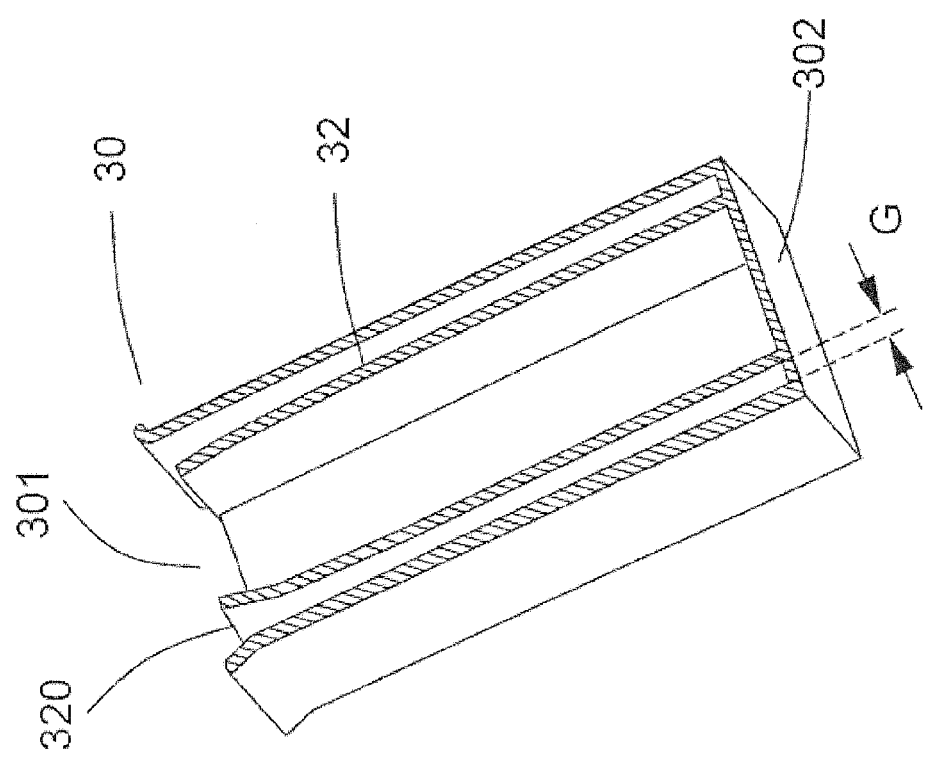
FIG. 2 is a sectional view of the dispensing container according to the first preferred embodiment of the present invention, showing a supporter lengthwise sectioned.

According to first preferred embodiment, the FIG. 2 shows a supporter 30 lengthwise sectioned. The supporter 30 is designed to be assembled with the dispensing container 20. The supporter 30 includes a pair of guiding portions 32 extending lengthwise from a bottom 302 of the supporter 30 to an open portion 301 thereof. Therein, each of the guiding portions 32 has a chamfered portion 320 adjacent to the open portion 301 for guiding the dispensing container to be smoothly mounted on the supporter 30. Please refer to FIG. 3 to see a friction F generated by the assembly between the dispensing container 20 and the supporter 30.

Figure 1C:
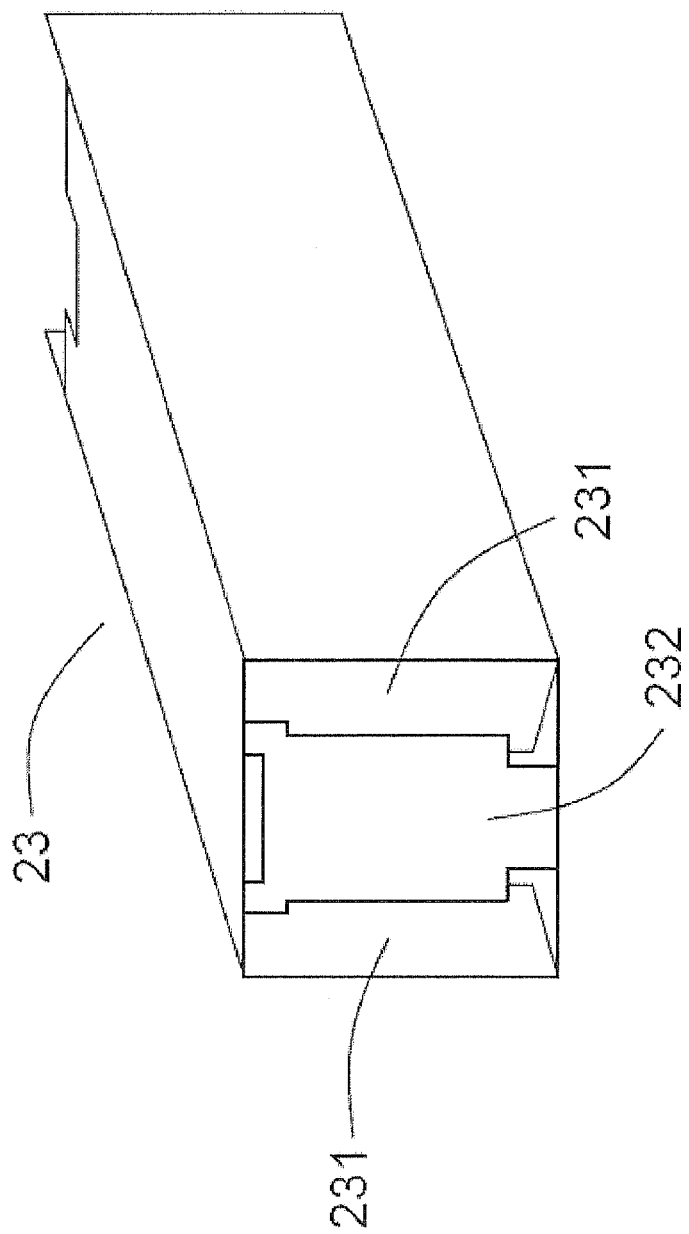
FIG. 1C is a bottom perspective view of the dispensing container according to the first preferred embodiment of the present invention, showing a base of the dispensing container.
Figure 3:
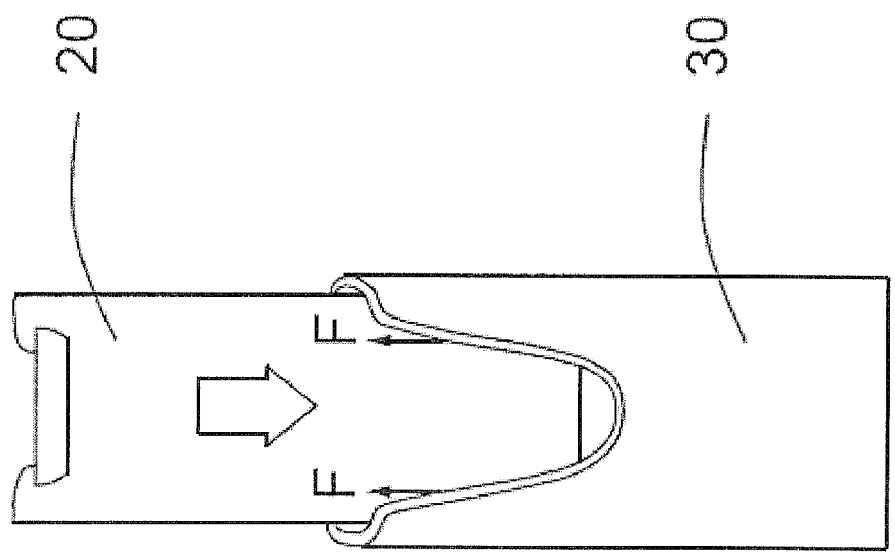
FIG. 3 is a schematic drawing according to the first preferred embodiment of the present invention, showing the friction generated upon the dispensing container being assembled with the supporter.

Referring now to FIG. 1C, FIG. 2, and FIG. 3, when the dispensing container 20 is pushed downward along the lengthwise direction of the supporter 30, outer surfaces of the guiding portions 32 and inner surfaces of lateral walls of the tab portions 231 and the hollow body 21 come into contact and the friction F is generated thereby. When the contacting friction F is large enough, the assembled dispensing container 20 and the supporter 30 are secured from unintentionally disassembling. Hence, a predetermined interval G between the guiding portions 32 of the supporter 30 dominates the magnitude of the friction F. Moreover, in the case that the base 23 of the dispensing container 20 does not include any tab portion 231, when the dispensing container 20 is mounted on the supporter 30, as long as the contacting area between the outer surfaces of the guiding portions 32 and the inner surfaces of lateral walls of the hollow body 21 is large enough, the sufficient friction F can be generated to secure the assembled dispensing container and supporter from unintentionally separating.

Figure 4:
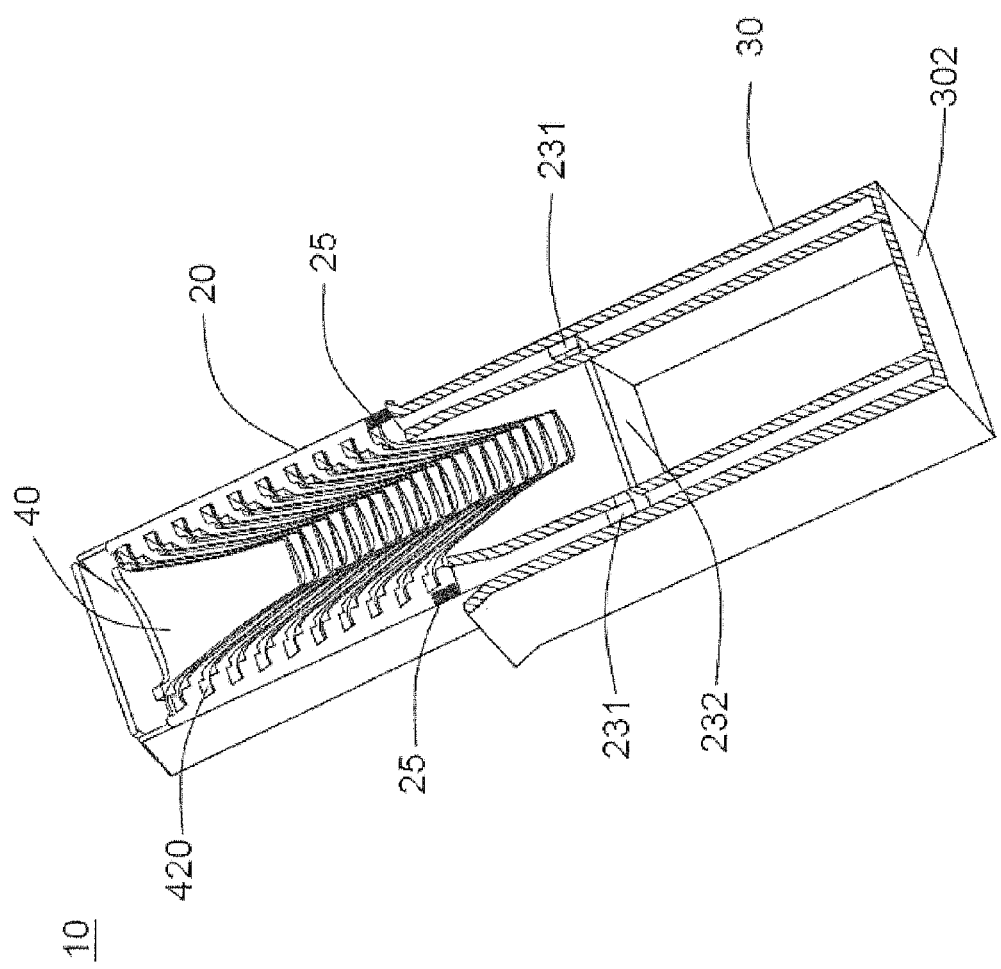
FIG. 4 is a schematic drawing according to a second preferred embodiment of the present invention, showing a dispensing assembly lengthwise sectioned.

Please refer to FIG. 4 for a second preferred embodiment of the present invention. Therein, a dispensing assembly 10 is lengthwise sectioned. The dispensing assembly 10 comprises a dispensing container 20 and a supporter 30. When the dispensing container 20 is mounted on the supporter 30, chamfered portions 320 of guiding portions 32 of the supporter 30 abut against the flange 420 of the bottommost ear thermometer probe cover 40. Referring to FIGS. 2 through 4, when the dispensing container 20 is pushed downward along the lengthwise direction of the supporter 30, the relative displacement between the dispensing container 20 and the supporter 30 takes place and makes the chamfered portions 320 of the guiding portions 32 push the aligned ear thermometer probe covers 40 in the dispensing container 20 toward the access opening, thereby facilitating access of the ear thermometer probe covers. Meantime, a pair of retaining portions 25 are provided at the opposite inner lateral walls of the hollow body 21 of the dispensing container 20 for retaining the flange 420 of the bottommost ear thermometer probe covers 40.

In the second preferred embodiment, the dispensing container 20, the supporter 30, and other related components included in the dispensing assembly 10 have the structures, materials, connecting means, and operational means similar to those of their counterparts described in the first preferred embodiment.

What is claimed is:

1. A dispensing container accommodating a plurality of stacked ear thermometer probe covers and being mounted on a supporter, the dispensing container comprising a hollow body for accommodating the plurality of stacked ear thermometer probe covers, the hollow body having one end formed with an access opening for allowing a probe of an ear thermometer to insert into an upmost probe cover in the hollow body, and having another end opposite to the access opening formed with a base, each of the ear thermometer probe covers having a close end and an open end opposite to the close end, the ear thermometer probe covers being such stacked and accommodated in the hollow body that the open ends thereof are posed to face the access opening, and each of the ear thermometer probe covers having the open end provided with at least a flange that radially extends outward from the open end, wherein the dispensing container is characterized in:

the flange of each of the ear thermometer probe covers has a diameter;

the hollow body has four lateral walls and is made of a flexible material and has a substantially rectangular transverse section with each of two opposite edges of the substantially rectangular transverse section having a length smaller than the diameter of the flange;

the four walls of the hollow body restorably deforms to tangentially touch the flange of each of the ear thermometer probe covers so as to keep the ear thermometer probe covers securely in the hollow body;

the supporter further comprising a pair of guiding portions and the pair of guiding portions being extending lengthwise from a bottom of the supporter to an open portion of the supporter and each of the guiding portions having a chamfered portion adjacent to the open portion; and the base of the hollow body further including a pair of tab portions, the pair of tab portions being bent toward the hollow body;

when the dispensing container is mounted on the supporter, inner surfaces of lateral walls of the hollow body of the dispensing container contact with outer surfaces of the guiding portions of the supporter, and the pair of tab portions contact outer surfaces of the guiding portions of the supporter, and the chamfered portions of guiding portions of the supporter abut against the flange of a bottommost one of the ear thermometer probe covers; and when the dispensing container is pushed downward along a lengthwise direction of the supporter, a relative displacement between the dispensing container and the supporter takes place and makes the chamfered portions of the guiding portions push the ear thermometer probe covers in the dispensing container toward the access opening.

2. The dispensing container of claim 1, wherein the base of the hollow body further comprises a lower cover to prevent the close end of the bottommost one of the ear thermometer probe covers from being directly exposed outside and getting contaminated.

3. The dispensing container of claim 1, further comprising an upper cover for shielding the access opening so as to prevent the ear thermometer probe covers from being directly exposed outside and getting contaminated.

4. The dispensing container of claim 1, wherein a pair of retaining portions are provided at opposite inner surfaces of lateral walls of the hollow body of the dispensing container for retaining the flange of the bottommost one of the ear thermometer probe covers.

5. The dispensing container of claim 1, wherein the flexible material of the hollow body is paper or plastic.

6. A dispensing assembly, comprising:

a plurality of stacked ear thermometer probe covers with each having a close end and an open end opposite to the close end, the open end being provided with at least a flange that radially extends outward from the open end, the flange having a diameter;

a dispensing container including a hollow body having one end formed with an access opening for allowing a probe of an ear thermometer to insert into one of the probe covers positioned in the hollow body, and having another end opposite to the access opening formed with a base, the ear thermometer probe covers being such stacked and accommodated in the hollow body that the open ends thereof are posed to face the access opening;

a supporter, including a pair of guiding portions extending lengthwise from a bottom of the supporter to an open portion of the supporter for guiding the dispensing container, and each of the guiding portions having one end to form a chamfered portion;

wherein the hollow body has four lateral walls and is made of a flexible material and has a substantially rectangular transverse section with each of two opposite edges of the substantially rectangular transverse section having a length smaller than the diameter of the flange; the four walls of the hollow body restorably deforms to tangentially touch the flange of each of the ear thermometer probe covers; and the base of the hollow body further includes a pair of tab portions, and the pair of tab portions are bent toward the hollow body;

the dispensing container is mounted on the supporter, and inner surfaces of lateral walls of the hollow body of the dispensing container contact with outer surfaces of the guiding portions of the supporter, and the tab portions contact outer surfaces of the guiding portions of the supporter, and the chamfered portions of guiding portions of the supporter abut against the flange of a bottommost one of the ear thermometer probe covers; and when the dispensing container is pushed downward along a lengthwise direction of the supporter, a relative displacement between the dispensing container and the supporter takes place and makes the chamfered portions of the guiding portions push the ear thermometer probe covers in the dispensing container toward the access opening.

7. The dispensing assembly of claim 6, wherein an interval between the guiding portions is determined by a predetermined friction.

8. The dispensing assembly of claim 6, wherein the base of the hollow body further comprises a lower cover to prevent the close end of the bottommost one of the ear thermometer probe covers from being directly exposed outside and getting contaminated.

9. The dispensing assembly of claim 6, further comprising an upper cover for shielding the access opening so as to prevent the ear thermometer probe covers from being directly exposed outside and getting contaminated.

10. The dispensing assembly of claim 6, wherein a pair of retaining portions are provided at opposite inner surfaces of lateral walls of the hollow body of the dispensing container for retaining the flange of the bottommost one of the ear thermometer probe covers.

11. The dispensing assembly of claim 6, wherein the flexible material of the hollow body is paper or plastic.

* * * * *